US009945794B2

(12) United States Patent
Zeng et al.

(10) Patent No.: US 9,945,794 B2
(45) Date of Patent: Apr. 17, 2018

(54) INSPECTION SYSTEMS AND METHODS FOR SYNCHRONOUSLY POSITIONING RADIOACTIVE MATERIAL (71) Applicant: Nuctech Company Limited, Beijing (CN)

(72) Inventors: Lei Zeng, Beijing (CN); Qiang Wang, Beijing (CN); Long Du, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 182 days.

(21) Appl. No.: 14/932,054

(22) Filed: Nov. 4, 2015

(65) Prior Publication Data
US 2016/0123901 A1    May 5, 2016

(30) Foreign Application Priority Data
Nov. 5, 2014 (CN) .......................... 2014 1 0616368

(51) Int. Cl.
*G01N 23/04* (2006.01)
*G01V 5/00* (2006.01)

(52) U.S. Cl.
CPC ............ *G01N 23/04* (2013.01); *G01V 5/0016* (2013.01); *G01V 5/0066* (2013.01); *G01V 5/0075* (2013.01)

(58) Field of Classification Search
CPC ........ G01N 23/00; G01N 23/02; G01N 23/04; G01N 23/083; G01V 5/00; G01V 5/0066; G01V 5/0008; G01V 5/0016
(Continued)

(56) References Cited

U.S. PATENT DOCUMENTS 8,295,433 B2 * 10/2012 Linev ................... G01V 5/0033
378/205
2004/0256565 A1    12/2004 Adams et al.
(Continued)

FOREIGN PATENT DOCUMENTS

CN         1598553 A      3/2005
CN      101210894 A      7/2008
(Continued)

OTHER PUBLICATIONS

Extended (Supplementary) European Search Report dated Mar. 16, 2016, issued in counterpart European Patent Application No. 15191658.2. (9 pages).
(Continued)

*Primary Examiner* — Jurie Yun
(74) *Attorney, Agent, or Firm* — Westerman, Hattori, Daniels & Adrian, LLP (57) ABSTRACT

A scanning and imaging apparatus comprises a ray source configured to generate an X-ray and a detection device configured to receive an X-ray transmitted through an inspected object, wherein the ray source is configured to image the inspected object by emitting the X-ray to the inspected object. A radioactivity detector is configured to detect whether the inspected object comprises radioactive material synchronously with the process of scanning implemented by the scanning and imaging apparatus. In a case that the radioactivity detector detects radioactive material, an actual position of the radioactive material in an X-ray image of the inspected object obtained by the scanning and imaging apparatus is marked in the image. The above solutions improve the accuracy of displaying the position of the radioactive source in the X-ray image. Further, inspection of radioactive material can be implemented while scanning an image.

15 Claims, 3 Drawing Sheets

(58) Field of Classification Search
USPC .............................. 378/57, 62, 98, 98.2, 162
See application file for complete search history.

(56) References Cited

U.S. PATENT DOCUMENTS

| | | |
|---|---|---|
| 2005/0105681 A1 | 5/2005 | Kang et al. |
| 2006/0210007 A1* | 9/2006 | Koskelo ............... G01V 5/0091 376/156 |
| 2011/0193711 A1 | 8/2011 | Faugier et al. |
| 2011/0274242 A1 | 11/2011 | Linev |

FOREIGN PATENT DOCUMENTS

| | | |
|---|---|---|
| CN | 201196635 Y | 2/2009 |
| CN | 104040374 A | 9/2014 |
| CN | 204374108 U | 6/2015 |
| WO | 2009/150416 A2 | 12/2009 |

OTHER PUBLICATIONS

Office Action and Search Report dated Jun. 2, 2016, issued in counterpart Chinese Patent Application No. 201410616368.0. (7 pages).

* cited by examiner

WIDTH OF A PULSE
FROM AN ACCELERATOR

DURATION OF RM
DETECTION

INSPECTION SYSTEMS AND METHODS FOR SYNCHRONOUSLY POSITIONING RADIOACTIVE MATERIAL

CROSS-REFERENCE TO RELATED APPLICATION(S)

This application claims priority to the Chinese Patent Application No. 201410616368.0, filed on Nov. 5, 2014, entitled "INSPECTION SYSTEMS AND METHODS FOR SYNCHRONOUSLY POSITIONING RADIOACTIVE MATERIAL" which is incorporated herein by reference in its entirety.

TECHNICAL FIELD

The present disclosure relates to a process of scanning and imaging a moving object, and in particular, to methods and systems for positioning radioactive material in the process of scanning and imaging.

BACKGROUND

An inspection system for imaging a vehicle using an X-ray is used for vehicle inspection. Specifically, an X-ray is transmitted through a vehicle to be scanned, to form an X-ray image of the vehicle, and an inspector may inspect inner details of the vehicle through the X-ray image without contact with the vehicle and damage to the vehicle. That is, the inspector can view goods loaded in a container without opening the container. A system for inspecting radioactive material is used to inspect radioactive material hidden in the inspected vehicle by means of inactive detection. Specifically, when the vehicle passes through the inspection system, if there is radioactive material, the inspection system may raise an alarm, and provides an approximate position of the radioactive material in the vehicle.

In practical applications in the field, the vehicle firstly passes through the system for inspecting Radioactive Material (RM) for inspecting whether radioactive material exist, and then is scanned by using an X-ray. When the radioactive material is inspected, the detection of the radioactive material starts when the vehicle arrives at the X-ray scanning and imaging apparatus, and ends after the vehicle completely passes through the scanning and imaging apparatus. A movement speed of the vehicle is calculated according to a time during which a probe is shielded and a length of the vehicle, to finally deduce a specific position of the radioactive material in the vehicle. The procedure comprises a warning start process, a warning peak process, and a warning end process. The above information is passed to the X-ray inspection system via an interface. In the X-ray image inspection system, when a beam is emitted by an accelerator, a detector starts to collect data, and when the accelerator stops emitting the beam, the detector stops collection and stores a complete image. The X-ray image is related to a scanning start time and a scanning end time of the device, a beam emission frequency of the current scanning, and a movement speed of the scanning device. The X-ray inspection system maps the position of the radioactive material in an inspection result of the radioactive material to an X-ray image. When the image is inspected, the specific position of the radioactive material in the vehicle can be intuitionally viewed, so as to facilitate a person who unpacks the container to rapidly find the radioactive source.

In practical applications, when scanning is implemented by using an X-ray, it is generally the case that a beam is firstly emitted and a scanning device starts to be moved to scan the inspected vehicle only after a dosage of the accelerator is stable. Therefore, there are some values of the air in the front of the X-ray image, instead of scanning the vehicle at the beginning. In addition, due to the position where the scanned vehicle is parked, when scanning is implemented, there may be large white spaces before or after the vehicle is scanned, and thus, the leftmost portion or the rightmost portion of the X-ray scanned image do not belong to the scanned vehicle. The detection of the radioactive material starts from the head of the vehicle, to provide a specific position of the radioactive material in the vehicle. As the starting points of the two inspection processes are different, the accurate position of the scanned vehicle in the X-ray image cannot be determined by the X-ray inspection system, which can only use the starting position of the image as a position of the head of the vehicle. Therefore, when the RM inspection result is mapped to the X-ray image, as the starting points of the two inspection processes are different and compression ratios of the two inspection images are different, a large deviation may be generated. Further, when the vehicle passes through the system for inspecting radioactive material, if the vehicle does not move at a constant speed, the result of the speed of the vehicle which is calculated by the RM system will also be influenced, which in turns influences the inspection result.

Further, as the two systems operate independently, an error in one-to-one correspondence between the inspection results of the two systems may be generated. In practical applications, many trucks may pass through a RM inspection system in sequence, and some inspection results may generated. Then, when the trucks pass through the X-ray inspection system, an order of these trucks may be changed for inspection, or some vehicles may directly be driven away without X-ray inspection. In this case, there may be a problem that an error occurs in the correspondence between the X-ray inspection image and the RM result.

SUMMARY

In view of the problems in the related art, a system and method for positioning radioactive material are proposed.

In an aspect of the present disclosure, an inspection system for positioning radioactive material is provided, comprising: a scanning and imaging apparatus comprising a ray source configured to generate an X-ray and a detection device configured to receive an X-ray transmitted through an inspected object, wherein the ray source is configured to image the inspected object by emitting the X-ray to the inspected object; and a radioactivity detector configured to detect whether the inspected object comprises radioactive material synchronously with the process of scanning implemented by the scanning and imaging apparatus, wherein in a case that the radioactivity detector detects radioactive material, an actual position of the radioactive material in an X-ray image of the inspected object obtained by the scanning and imaging apparatus is marked in the image.

According to some embodiments, the radioactivity detector is arranged to be located at a predetermined distance from a main beam from the ray source in a movement direction of the inspected object.

According to some embodiments, while the scanning and imaging apparatus starts to scan the inspected object, the radioactivity detector starts to detect and record a scanning start time; and when radioactive material is detected, the radioactivity detector transmits a time interval from a time when the radioactive material is detected to the scanning start time to the scanning and imaging apparatus as a warning start time of the radioactive material, and when it is detected that the radiation of the radioactive material ends, the radioactivity detector transmits a warning peak time and a warning end time to the scanning and imaging apparatus respectively, and then the scanning and imaging apparatus calculates the actual position of the radioactive material in the image of the inspected object based on the scanning start time, the warning start time, the warning peak time, and the warning end time; wherein the warning peak time is a time interval from a time when a peak value of the radioactive material is detected by the radioactivity detector to the scanning start time, and the warning end time is a time interval from a time when no radioactive material is detected by the radioactivity detector to the scanning start time.

According to some embodiments, a sensor which is arranged in a corresponding position in a scanning plane of the ray source of the scanning and imaging apparatus is configured to determine that the inspected object has been scanned.

According to some embodiments, the scanning and imaging apparatus and the radioactivity detector are controlled by a synchronous signal to operate synchronously, or a high voltage is applied to the ray source to trigger the radioactivity detector to start to operate.

According to some embodiments, the scanning start time is denoted as T1, the scanning end time is denoted as T2, and a period of time during which the whole scanning image is obtained is denoted as T; the scanning and imaging apparatus obtains warning start information, warning peak information, and warning end information of the radioactive material from the radioactivity detector, which are denoted as Ts, Tm and Te respectively, wherein Ts, Tm and Te are time intervals from the warning start time, the warning peak time, and the warning end time to the scanning start time T1 respectively; ratios between the warning start, the warning peak, and the warning end in the whole scanning process are obtained by calculating Ts/T, Tm/T, and Te/T; after the scanning implemented by the scanning and imaging apparatus ends, a total number of columns N is obtained from the detection device thereof, and is multiplied with the above various ratios Ts/T, Tm/T, and Te/T, to obtain numbers of columns Ns, Nm, and Ne corresponding to the respective warning start, warning peak, and warning end in the image; and the corresponding positions of the warning start, the warning peak, and the warning end in the image are obtained respectively by shifting Ns, Nm, and Ne columns from the corresponding position of the scanning start time T1 in the image along an image formation direction.

According to some embodiments, the above numbers of columns Ns, Nm, and Ne of the warning start, the warning peak, and the warning end are corrected or the corresponding position of the scanning start time T1 in the image is corrected based on a distance between the radioactivity detector and the detection device of the scanning and imaging apparatus in a relative movement direction.

According to some embodiments, the radioactivity detector implements radioactivity detection in a time interval between two pulses of rays emitted by the ray source, to avoid interference to the ray source.

According to some embodiments, the system further comprises a speed sensor configured to measure a speed of the inspected object in the detection process in a case that the scanning and imaging apparatus is static and the inspected object moves, wherein the scanning and imaging apparatus is configured to control reconstruction of the scanned image according to a movement speed related to the inspected object received from the speed sensor, and modify the data of the scanned image according to the movement speed.

According to some embodiments, the inspected object moves at a predetermined speed relative to the system, and if the inspected object moves at an upper limit of the range of the predetermined speed, the scanning and imaging apparatus implements sampling at a beam emission frequency of the ray source; and if the inspected object moves at a speed lower than the upper limit of the range of the predetermined speed, the scanning and imaging apparatus is in a sub-sampling state, and the image is reconstructed by using an interpolation method or convolution method.

In another aspect of the present disclosure, a method for positioning radioactive material is provided, comprising steps of: imaging an inspected object by using a scanning and imaging apparatus comprising a ray source configured to generate an X-ray and a detection device configured to receive an X-ray transmitted through the inspected object, wherein the ray source is configured to image the inspected object by emitting the X-ray to the inspected object; and detecting whether the inspected object comprises radioactive material synchronously with the process of scanning implemented by the scanning and imaging apparatus, wherein in a case that the radioactivity detector detects radioactive material, an actual position of the radioactive material in an X-ray image of the inspected object obtained by the scanning and imaging apparatus is marked in the image.

The above solution solves the problem in the related art that the accuracy of positioning the radioactive material is not high enough, and improves the accuracy of displaying the position of the radioactive source in the X-ray image, i.e., reducing a deviation generated due to a scanning manner or the like when an inspection result of the radioactive material is mapped to the X-ray image.

Further, according to the above solutions, inspection of radioactive material can be implemented while scanning an image. In this way, an error in the correspondence between inspection results of two systems when the two systems operate independently is avoided.

BRIEF DESCRIPTION OF THE DRAWINGS

For better understanding the present disclosure, embodiments of the present disclosure will be described according to the following accompanying drawings.

Not all circuits or structures according to the embodiments are displayed in the accompanying drawings.

Throughout all accompanying drawings, the same reference signs represent the same or similar components or features.

DETAILED DESCRIPTION

Specific embodiments of the present invention will be described below in detail. It should be noted that the embodiments described herein are illustrated merely by way of example instead of limiting the present invention. In the following description, numerous specific details are set forth in order to provide a thorough understanding of the present invention. However, it is obvious to those skilled in the art that the present invention may be practiced without these specific details. In other instances, well known circuits, materials or methods have not been described in detail to avoid obscuring the present invention.

Reference throughout this specification to "one embodiment", "an embodiment", "one example" or "an example" means that a particular feature, structure, or characteristic described in connection with the embodiment or example is included in at least one embodiment of the present invention. Thus, the appearances of the phrase "in one embodiment", "in an embodiment", "one example" or "an example" in various places throughout this specification are not necessarily all referring to the same embodiment or example. Furthermore, the particular features, structures, or characteristics may be combined in any suitable combination and/or sub-combination in one or more embodiments or examples. In addition, those skilled in the art should understand that the accompanying drawings provided herein are illustrative, and are not necessarily drawn to scale. It should be understood that when an element is recited as being "coupled to" or "connected to" another element, the element can be directly coupled or coupled to the further element, or otherwise there may be an intervening element interposed therebetween. In contrary, when an element is recited as being "directly coupled to" or "directly connected to" another element, there is no intervening element interposed therebetween. The same reference numbers are used to refer to the same elements. A term "and/or" used herein comprises any or all combinations of one or more listed related items.

According to some embodiments of the present disclosure, in order to solve the problem in the related art that the accuracy of positioning the radioactive material is not high enough, a system for positioning radioactive material is provided, comprising a scanning and imaging apparatus and a radioactivity detector. The scanning and imaging apparatus comprises a ray source configured to generate an X-ray and a detection device configured to receive an X-ray transmitted through an inspected object, wherein the ray source is configured to image the inspected object by emitting the X-ray to the inspected object. The radioactivity detector is configured to detect whether the inspected object comprises radioactive material synchronously with the process of scanning implemented by the scanning and imaging apparatus. In a case that the radioactivity detector detects radioactive material, an actual position of the radioactive material in an X-ray image of the inspected object obtained by the scanning and imaging apparatus is marked in the image. Thus, when a moving object (i.e., an inspected object) such as a vehicle is inspected, in a case that there is radioactive material, the radioactive material is accurately positioned in the image of the object.

Figure 1A:
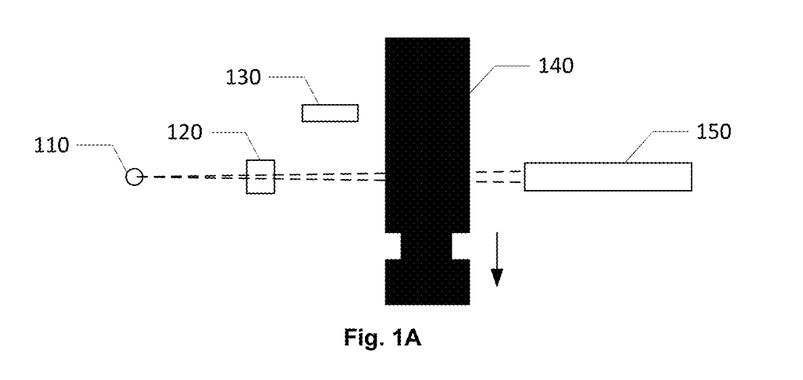
FIGS. 1A and 1B are structural diagrams of an inspection system according to an embodiment of the present disclosure.
Figure 1B:
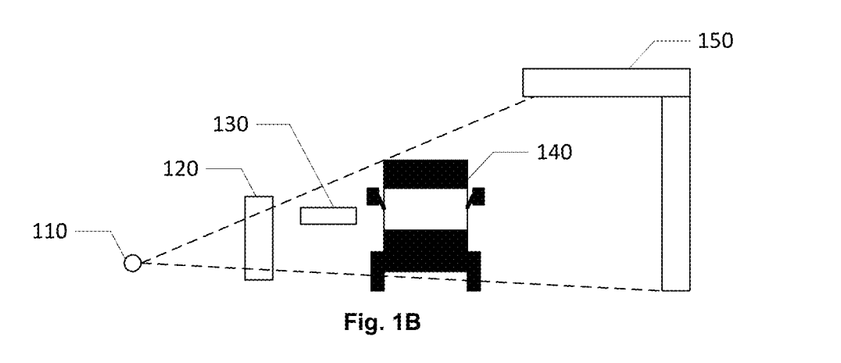

FIGS. 1A and 1B are structural diagrams of an inspection system according to an embodiment of the present disclosure. As shown in FIG. 1A, an X-ray is generated by a ray source 110, and is then collimated by a collimator 120 to implement security inspection of a moving truck 140. A ray transmitted through the truck is received by a detector 150, to obtain a transmission image. When the above inspection process is implemented, a configured RM detector 130 is further used to detect whether there is radioactive material in the truck 140. In a case that the RM detector 130 detects the radioactive material, an actual position of the radioactive material in the X-ray image of the truck 140 obtained by the scanning and imaging apparatus is marked in the image.

According to some embodiments, an operation manner of the existing system for inspecting radioactive material is changed, to merge the system for inspecting radioactive material into the operation flow of the X-ray image system, which solves the problem of deviation in the mapping between two inspection results. For example, when hardware is installed, the RM detector 130 is installed near a main beam from an accelerator (or other types of ray sources) as close as possible. In this way, it is ensured that the accelerator and the RM device (for example, a RM detector) can operate simultaneously to inspect the scanned vehicle during inspection, as shown in FIG. 1A. When X-ray scanning is implemented, the scanning may start from the head of the vehicle. In this case, the scanned vehicle firstly passes through the RM detection system, and then passes through the main beam of the accelerator. Alternatively, the scanning may also start from the end of the vehicle. In this case, the scanned vehicle firstly passes through the main beam of the accelerator, and then passes through the RM detection system.

Figure 2:
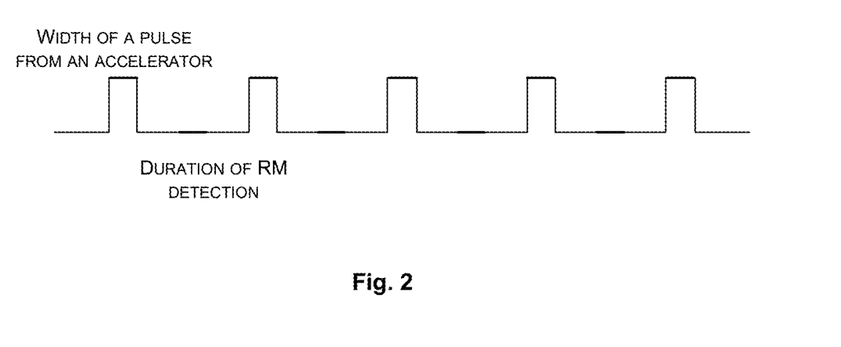
FIG. 2 illustrates a relationship between a pulse of a beam emitted by a ray source and an interval for RM detection.

In addition, in the process of implementing X-ray inspection and RM detection inspection, the accelerator and the RM detector 130 operate simultaneously, wherein the RM detector implements detection in a period of time between two pulses during which a beam is emitted by the accelerator, where in the period of time no beam is emitted by the accelerator, as shown in FIG. 2. In this way, the interference of the ray emitted by the accelerator to the RM detector is avoided. Each pulse time during which a beam is emitted by the accelerator is approximately a few microseconds. During this period of time, the accelerator may generate radiation, which influences the RM detection. The period of time between two pulses is a trigger period of the accelerator. By taking a beam emission frequency of 40 Hz as an example, the trigger period is approximately 25 milliseconds. The RM system may obtain a trigger timing of the accelerator through the accelerator triggering a signal line, and then avoids the trigger timing of the accelerator, for detection of the radioactive material.

In other embodiments, a sensor arranged in a corresponding position in a scanning plane of the ray source of the scanning and imaging apparatus may be used to determine that the inspected object has been scanned, or the scanning and imaging apparatus and the radioactivity detector are controlled by a synchronous signal to operate synchronously. Alternatively, in response to a high voltage applied to the ray source, the radioactivity detector is triggered to start to operate. Of course, synchronous control of the accelerator/ray source and the RM detector is not limited to the above methods, and all manners of enabling the accelerator/ray source and the RM detector to synchronously operate without interference are included within the protection scope of the present disclosure.

According to some embodiments, the position information of the radioactive material is not calculated by the RM system (including the RM detector), and instead, the RM detector merely transmits the time when the radioactive material is detected to the X-ray inspection system, which calculates an accurate position of the radioactive material in the X-ray image. For example, upon starting to scan the inspected vehicle, the X-ray inspection system transmits a command to notify the RM system. The RM system records a scanning start time, and when radioactive material is detected, the RM system transmits a time interval (in units of milliseconds) from a time when the radioactive material is detected to the scanning start time to the X-ray inspection system. When it is detected that the radiation of the radioactive material ends, the time when a peak of the radiation is detected and the time when the radiation ends (the time is a time interval starting from a time when the image starts to be scanned) are transmitted to the X-ray inspection system respectively.

Figure 3:
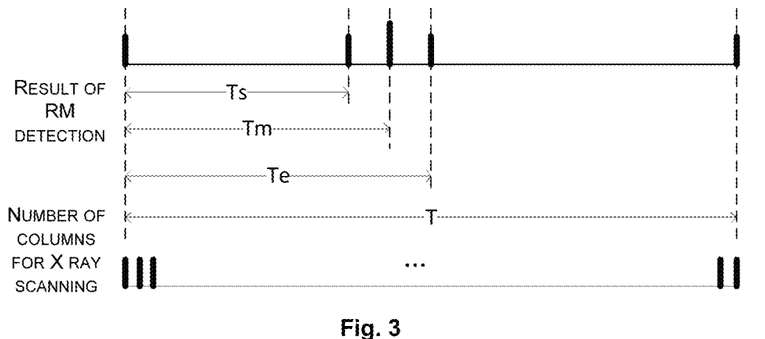
FIG. 3 illustrates a timing diagram of a process of positioning radio material according to an embodiment of the present disclosure.

Then, the X-ray inspection system calculates the position of the radioactive material by synthetically using various information. For example, the X-ray system knows the scanning start time and the scanning end time, and then obtains from the RM system a time interval from the time when the radioactive material is detected to the scanning start time, the beam emission frequency of the X-ray is unchanged and the scanning speed is also constant. Therefore, a correspondence relationship between the radioactive material and the X-ray image may be obtained, as shown in FIG. 3.

Figure 4:
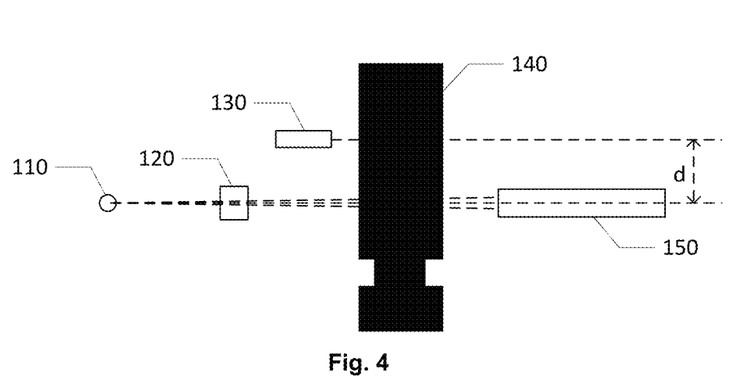
FIG. 4 illustrates a diagram of a relationship configured between a RM device and a scanning and imaging apparatus according to an embodiment of the present disclosure.

As the position where the RM device is installed may not be consistent with the position of the main beam of the accelerator, i.e., there is always a certain deviation. For example, Lo illustrated in FIG. 4 is a deviation between the two positions. When the peak of the radioactive material is detected by the RM device, i.e., the radioactive material is closest to the RM device, the position of the main beam from the accelerator is displayed in the X-ray scanned image. Further, since a time is transmitted by the RM device to the X-ray system as the warning information, the X-ray inspection system may consider at this time that there is radioactive material in the position of the main beam from the accelerator. In this case, there is a certain deviation Lo from the actual position of the radioactive material. Therefore, the deviation needs to be compensated in the process of calculation.

For example, a manner of calculating an accurate position by the X-ray inspection system is as follows.

Firstly, when the X-ray inspection system starts to scan, a current time T1 is recorded, and when the scanning ends, a current time T2 is recorded, so as to obtain the duration during which the image is scanned, i.e., T=T2−T1.

Secondly, the X-ray inspection system obtains warning start information, warning peak information, and warning end information of the radioactive material from the RM system, which is time intervals from the scanning start time (T1) in units of milliseconds. That is, durations from the warning start time, warning peak time, and warning end time to the scanning start time may be obtained, which are Ts, Tm and Te respectively.

Thirdly, ratios of the warning start, warning peak, and warning end in the whole scanning process may be obtained through Ts/T, Tm/T and Te/T.

Fourthly, after the scanning implemented by the scanning and imaging apparatus ends, a total number of columns N is obtained from the detection device, and is multiplied with the above various ratios Ts/T, Tm/T, and Te/T, to obtain numbers of columns Ns, Nm, and Ne corresponding to the respective warning start, warning peak, and warning end in the image respectively; and the corresponding positions of the warning start, the warning peak, and the warning end in the image are obtained respectively by shifting Ns, Nm, and Ne columns from the corresponding position of the scanning start time T1 in the image along an image formation direction. For example, after the scanning implemented by the X-ray inspection system ends, a total number of columns N of the scanning obtained from the detector may be known. The total number of columns may be multiplied with the various ratios obtained in the third step, to obtain numbers of columns Ns, Nm, and Ne corresponding to the respective warning start, warning peak, and warning end in the image. It should be noted that in this case, a deviation between the RM device and the main beam of the accelerator is not concerned with respect to the obtained number of columns.

Fifthly, a column of data of the X-ray scanned image corresponds to a physical size d of the object which is actually scanned. For example, if when a truck is scanned, an X-ray image with a total number of columns n is generated, a corresponding length of the truck which is actually scanned is approximately n*d. A value of d is previously written into a database, for use by the whole X-ray scanning system.

Sixthly, the above numbers of columns Ns, Nm, and Ne of the warning start, the warning peak, and the warning end are corrected or the corresponding position of the scanning start time T1 in the image and/is corrected based on a distance between the radioactivity detector and the detection device of the scanning and imaging apparatus in a relative movement direction. For example, as shown in FIG. 4, a physical distance Lo between a RM probe and the main beam of the accelerator is previously measured. If the scanning is implemented from the head of the vehicle to the end of the vehicle, the warning start position is Ls=Ns*d+Lo, the warning peak position is Lm=Nm*d+Lo, and the warning end position is Le=Ne*d+Lo. If the scanning is implemented from the end of the vehicle to the head of the vehicle, the warning start position is Ls=Ns*d−Lo, the warning peak position is Lm=Nm*d−Lo, and the warning end position is Le=Ne*d−Lo. The position information is recorded in the database.

According to the above embodiments, when the X-ray scanning is implemented, radioactive material is inspected at the same time, which solves the problem of one-to-one correspondence between the inspection results of the two systems. In addition, positioning is implemented according to a beam emission time of the accelerator, and a space of the air which is scanned before the head of the vehicle and after the end of the vehicle is also calculated, without applying limitations to the X-ray scanning. Conventionally, beam emission needs to start at the head of the vehicle, and end at the end of the vehicle. In practical applications, the operation is difficult to implement. Further, the movement speed of the scanning device is stable, which avoids an error in speed measurement implemented by the RM device. At the same time, information such as the speed of the vehicle, the frequency, and the crystal of the detector or the like are taken into consideration, which improves the accuracy.

Figure 5:
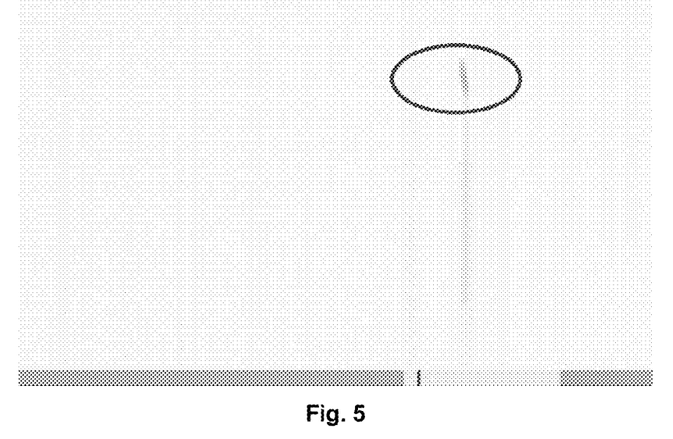
FIG. 5 illustrates an example of an image obtained in a system according to an embodiment of the present disclosure.

FIG. 5 illustrates a structural diagram of a system according to an embodiment of the present disclosure. As shown in FIG. 5, a red circle represents a radioactive source. A green strip portion below the image represents RM warning information, wherein green means safety, yellow means RM warning, and red means warning peak, i.e., the position of the radioactive source.

Figure 6:
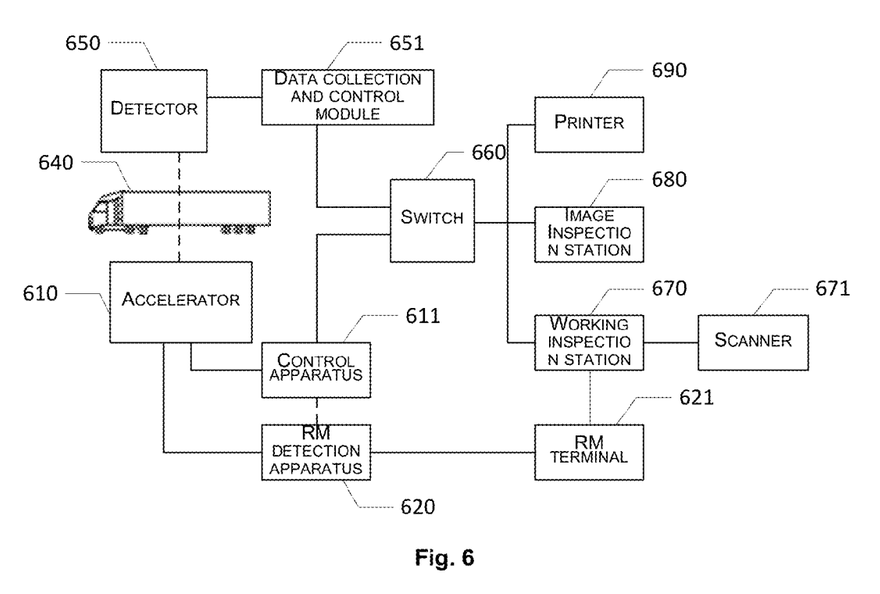
FIG. 6 illustrates a structural diagram of a system according to an embodiment of the present disclosure.

FIG. 6 illustrates a diagram of deployment of a system according to an embodiment of the present disclosure. As shown in FIG. 6, an accelerator 610 and a detector 650 are hardware devices, a data collection and control module 651 is connected to the detector 650 and controls the detector 650, a control apparatus 611 is connected to the accelerator 610 and controls the accelerator 610 to emit a beam and stop emitting the beam, and a RM detection apparatus 620 is connected to the accelerator 610 to obtain related control information. An image inspection station 680 and a working inspection station 670 are workstations which are matched with the scanning device, and are connected to the data collection and control module 651 via a switch 660 for communication. An image result may be printed by a printer 690. A scanner 671 is connected to the working inspection station 670. A RM terminal 621 is connected to the working inspection station 670, and is connected to the RM detection apparatus 620 via a hardware connection line. The RM terminal may also be in communication with the working inspection station via the switch.

With the above system, in some embodiments, the accelerator 610 generates an X-ray, and an X-ray which is transmitted through an inspected object is received by the detector 650 for imaging the inspected object. A radioactivity detector such as the RM detection apparatus 620 detects whether the inspected object comprises radioactive material synchronously with the scanning process of the scanning and imaging apparatus which comprises the accelerator 610, the detector 650 and the data collection and control module 651. In a case that the radioactivity detector detects radioactive material, an actual position of the radioactive material in an X-ray image of the inspected object obtained by the scanning and imaging apparatus is marked in the image. Thus, when a moving object such as a vehicle is inspected, in a case that there is radioactive material, the radioactive material is accurately positioned in the image of the object.

In addition, in other embodiments, a speed sensor may also be configured to measure a speed of a truck in the detection process in a case that the scanning and imaging apparatus is static and the truck moves. The scanning and imaging apparatus is configured to control reconstruction of the scanned image according to a movement speed related to the truck received from the speed sensor, and modify the data of the scanned image according to the movement speed. For example, the truck moves at a predetermined speed relative to the system. If the truck moves at an upper limit of the range of the predetermined speed, the scanning and imaging apparatus implements sampling at a beam emission frequency of the ray source; and if the truck moves at a speed lower than the upper limit of the range of the predetermined speed, the scanning and imaging apparatus is in a sub-sampling state, and the image is reconstructed by using an interpolation method or convolution method.

The foregoing detailed description has set forth various embodiments of the system and method for positioning radioactive material via the use of diagrams, flowcharts, and/or examples. In a case that such diagrams, flowcharts, and/or examples contain one or more functions and/or operations, it will be understood by those skilled in the art that each function and/or operation within such diagrams, flowcharts or examples may be implemented, individually and/or collectively, by a wide range of structures, hardware, software, firmware, or virtually any combination thereof. In one embodiment, several portions of the subject matter described in the embodiments of the present disclosure may be implemented via Application Specific Integrated Circuits (ASICs), Field Programmable Gate Arrays (FPGAs), Digital Signal Processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of those skilled in the art in ray of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

While the present disclosure has been described with reference to several typical embodiments, it is apparent to those skilled in the art that the terms are used for illustration and explanation purpose and not for limitation. The present disclosure may be practiced in various forms without departing from the spirit or essence of the present disclosure. It should be understood that the embodiments are not limited to any of the foregoing details, and shall be interpreted broadly within the spirit and scope as defined by the following claims. Therefore, all of modifications and alternatives falling within the scope of the claims or equivalents thereof are to be encompassed by the claims as attached.

We claim:

1. An inspection system for synchronously positioning radioactive material, comprising:
a scanning and imaging apparatus comprising a ray source configured to generate an X-ray and a detection device configured to receive an X-ray transmitted through an inspected object, wherein the ray source is configured to image the inspected object by emitting the X-ray to the inspected object; and
a radioactivity detector configured to detect whether the inspected object comprises radioactive material synchronously with the process of scanning implemented by the scanning and imaging apparatus,
wherein in a case that the radioactivity detector detects radioactive material, an actual position of the radioactive material in an X-ray image of the inspected object obtained by the scanning and imaging apparatus is marked in the image;
wherein while the scanning and imaging apparatus starts to scan the inspected object, the radioactivity detector starts to detect and record a scanning start time; and when radioactive material is detected, the radioactivity detector transmits a time interval from a time when the radioactive material is detected to the scanning start time to the scanning and imaging apparatus as a warning start time of the radioactive material, and when it is detected that a radiation of the radioactive material ends, the radioactivity detector transmits a warning peak time and a warning end time to the scanning and imaging apparatus respectively, and then the scanning and imaging apparatus calculates the actual position of the radioactive material in the image of the inspected object based on the scanning start time, the warning start time, the warning peak time, and the warning end time; wherein the warning peak time is a time interval from a time when a peak value of the radioactive material is detected by the radioactivity detector to the scanning start time, and the warning end time is a time interval from a time when no radioactive material is detected by the radioactivity detector to the scanning start time.

2. The system according to claim 1, wherein the radioactivity detector is arranged to be located at a predetermined distance from a main beam from the ray source in a movement direction of the inspected object.

3. The system according to claim 1, wherein a sensor which is arranged in a corresponding position in a scanning plane of the ray source of the scanning and imaging apparatus is configured to determine that the inspected object has been scanned, or the scanning and imaging apparatus and the radioactivity detector are controlled by a synchronous signal to operate synchronously, or a high voltage is applied to the ray source to trigger the radioactivity detector to start to operate.

4. The system according to claim 1, wherein,
the scanning start time is denoted as T1, a scanning end time is denoted as T2, and a period of time during which the whole scanning image is obtained is denoted as T;
the scanning and imaging apparatus obtains warning start information, warning peak information, and warning end information of the radioactive material from the radioactivity detector, which are denoted as Ts, Tm and Te respectively, wherein Ts, Tm and Te are time intervals from the warning start time, the warning peak time, and the warning end time to the scanning start time T1 respectively;
ratios between the warning start, the warning peak, and the warning end in the whole scanning process are obtained by calculating Ts/T, Tm/T, and Te/T;
after the scanning implemented by the scanning and imaging apparatus ends, a total number of columns N is obtained from the detection device thereof, and is multiplied with the ratios Ts/T, Tm/T, and Te/T, to obtain numbers of columns Ns, Nm, and Ne corresponding to the respective warning start, warning peak, and warning end in the image; and the corresponding positions of the warning start, the warning peak, and the warning end in the image are obtained respectively by shifting Ns, Nm, and Ne columns from the corresponding position of the scanning start time T1 in the image along an image formation direction.

5. The system according to claim 4, wherein numbers of columns Ns, Nm, and Ne of the warning start, the warning peak, and the warning end are corrected or the corresponding position of the scanning start time T1 in the image is corrected based on a distance between the radioactivity detector and the detection device of the scanning and imaging apparatus in a relative movement direction.

6. The system according to claim 1, wherein the radioactivity detector implements radioactivity detection in a time interval between two pulses of rays emitted by the ray source, to avoid interference to the ray source.

7. The system according to claim 1, further comprising a speed sensor configured to measure a speed of the inspected object in the detection process in a case that the scanning and imaging apparatus is static and the inspected object moves, wherein the scanning and imaging apparatus is configured to control reconstruction of the scanned image according to a movement speed related to the inspected object received from the speed sensor, and modify the data of the scanned image according to the movement speed.

8. The system according to claim 7, wherein the inspected object moves at a predetermined speed relative to the system, and if the inspected object moves at an upper limit of a range of the predetermined speed, the scanning and imaging apparatus implements sampling at a beam emission frequency of the ray source; and if the inspected object moves at a speed lower than the upper limit of the range of the predetermined speed, the scanning and imaging apparatus is in a sub-sampling state, and the image is reconstructed by using an interpolation method or convolution method.

9. A method for positioning radioactive material, comprising steps of:
imaging an inspected object by using a scanning and imaging apparatus comprising a ray source configured to generate an X-ray and a detection device configured to receive an X-ray transmitted through the inspected object, wherein the ray source is configured to image the inspected object by emitting the X-ray to the inspected object; and detecting, by a radioactivity detector, whether the inspected object comprises radioactive material synchronously with the process of scanning implemented by the scanning and imaging apparatus, wherein in a case that the radioactivity detector detects radioactive material, an actual position of the radioactive material in an X-ray image of the inspected object obtained by the scanning and imaging apparatus is marked in the image;

wherein while the scanning and imaging apparatus starts to scan the inspected object, the radioactivity detector starts to detect and record a scanning start time; and when radioactive material is detected, the radioactivity detector transmits a time interval from a time when the radioactive material is detected to the scanning start time to the scanning and imaging apparatus as a warning start time of the radioactive material, and when it is detected that a radiation of the radioactive material ends, the radioactivity detector transmits a warning peak time and a warning end time to the scanning and imaging apparatus respectively, and then the scanning and imaging apparatus calculates the actual position of the radioactive material in the image of the inspected object based on the scanning start time, the warning start time, the warning peak time, and the warning end time; wherein the warning peak time is a time interval from a time when a peak value of the radioactive material is detected by the radioactivity detector to the scanning start time, and the warning end time is a time interval from a time when no radioactive material is detected by the radioactivity detector to the scanning start time.

10. The method according to claim 9, wherein a sensor which is arranged in a corresponding position in a scanning plane of the ray source of the scanning and imaging apparatus is configured to determine that the inspected object has been scanned, or the scanning and imaging apparatus and the radioactivity detector are controlled by a synchronous signal to operate synchronously, or a high voltage is applied to the ray source to trigger the radioactivity detector to start to operate.

11. The method according to claim 10, wherein, the scanning start time is denoted as T1, a scanning end time is denoted as T2, and a period of time during which the whole scanning image is obtained is denoted as T;

the scanning and imaging apparatus obtains warning start information, warning peak information, and warning end information of the radioactive material from the radioactivity detector, which are denoted as Ts, Tm and Te respectively, wherein Ts, Tm and Te are time intervals from the warning start time, the warning peak time, and the warning end time to the scanning start time T1 respectively;

ratios between the warning start, the warning peak, and the warning end in the whole scanning process are obtained by calculating Ts/T, Tm/T, and Te/T;

after the scanning implemented by the scanning and imaging apparatus ends, a total number of columns N is obtained from the detection device thereof, and is multiplied with the ratios Ts/T, Tm/T, and Te/T, to obtain numbers of columns Ns, Nm, and Ne corresponding to the respective warning start, warning peak, and warning end in the image; and the corresponding positions of the warning start, the warning peak, and the warning end in the image are obtained respectively by shifting Ns, Nm, and Ne columns from the corresponding position of the scanning start time T1 in the image along an image formation direction.

12. The method according to claim 11, wherein numbers of columns Ns, Nm, and Ne of the warning start, the warning peak, and the warning end are corrected or the corresponding position of the scanning start time T1 in the image is corrected based on a distance between the radioactivity detector and the detection device of the scanning and imaging apparatus in a relative movement direction.

13. The method according to claim 9, wherein the radioactivity detector implements radioactivity detection in a time interval between two pulses of rays emitted by the ray source, to avoid interference to the ray source.

14. The method according to claim 9, further comprising measuring a speed of the inspected object in the detection process in a case that the scanning and imaging apparatus is static and the inspected object moves, controlling reconstruction of the scanned image according to a movement speed of the inspected object, and modifying the data of the scanned image according to the movement speed.

15. The method according to claim 14, wherein the inspected object moves at a predetermined speed relative to the apparatus, and if the inspected object moves at an upper limit of a range of the predetermined speed, sampling is implemented at a beam emission frequency of the ray source; and if the inspected object moves at a speed lower than the upper limit of the range of the predetermined speed, the image is reconstructed by using an interpolation method or convolution method.

* * * * *